(12) United States Patent
Vilsmeier et al.

(10) Patent No.: US 10,157,310 B2
(45) Date of Patent: Dec. 18, 2018

(54) MEDICAL TRACKING SYSTEM COMPRISING MULTI-FUNCTIONAL SENSOR DEVICE

(75) Inventors: Stefan Vilsmeier, Munich (DE); Christian Brack, NeusaB (DE); Ingmar Hook, Feldkirchen (DE); Timo Neubauer, Grasbrunn (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 14/349,466

(22) PCT Filed: Oct. 13, 2011

(86) PCT No.: PCT/EP2011/067935
§ 371 (c)(1),
(2), (4) Date: Apr. 3, 2014

(87) PCT Pub. No.: WO2013/053397
PCT Pub. Date: Apr. 18, 2013

(65) Prior Publication Data
US 2014/0247336 A1     Sep. 4, 2014

(51) Int. Cl.
*G06K 9/00* (2006.01)
*A61B 34/20* (2016.01)
(Continued)

(52) U.S. Cl.
CPC .......... *G06K 9/00369* (2013.01); *A61B 34/20* (2016.02); *A61B 17/154* (2013.01); *A61B 2017/00199* (2013.01); *A61B 2034/2048* (2016.02); *A61B 2034/2055* (2016.02); *A61B 2034/2057* (2016.02); *A61B 2034/2068* (2016.02); *A61B 2034/2072* (2016.02);
(Continued)

(58) Field of Classification Search
None
See application file for complete search history.

(56) References Cited

U.S. PATENT DOCUMENTS

| 6,119,033 A | 9/2000 | Spigelman et al. |
| 6,161,032 A | 12/2000 | Acker |

(Continued)

FOREIGN PATENT DOCUMENTS

WO     2013053398 A1     4/2013

OTHER PUBLICATIONS

International Search Report for International Application No. PCT/EP2011/067935 dated Jun. 19, 2012.
(Continued)

*Primary Examiner* — Kaitlin A Retallick
(74) *Attorney, Agent, or Firm* — Tucker Ellis LLP

(57) ABSTRACT

The present invention relates to a medical tracking system comprising at least one sensor device which can be positioned in a fixed position relative to a target, the sensor device comprising a marker device and a marker device detector, the marker device detector being capable of obtaining information for determining a relative position between the marker device detector and another marker device, the system further comprising a control unit configured to process a medical navigation workflow and to select the function of the sensor device as either acting as a marker device detector or as a marker device in a step of the medical navigation workflow.

24 Claims, 15 Drawing Sheets

Figure 1:
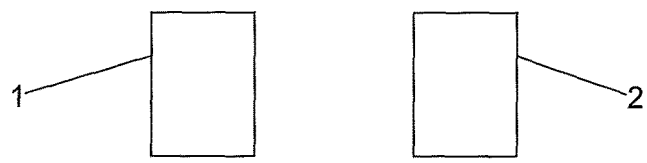

(51) Int. Cl.
*A61B 17/15* (2006.01)
*A61B 17/00* (2006.01)
*A61B 90/00* (2016.01)

(52) U.S. Cl.
CPC ............ *A61B 2090/3983* (2016.02); *A61B 2090/3995* (2016.02)

(56) References Cited

U.S. PATENT DOCUMENTS

| | | |
|---|---|---|
| 8,862,200 B2 | 10/2014 | Sherman et al. |
| 2001/0034530 A1 | 10/2001 | Malackowski et al. |
| 2004/0243148 A1 | 12/2004 | Wasielewski |
| 2005/0197569 A1* | 9/2005 | McCombs ............ A61B 17/154 600/426 |
| 2007/0078678 A1* | 4/2007 | DiSilvestro ............. G06F 19/00 705/2 |
| 2008/0180537 A1* | 7/2008 | Weinberg ............. H04N 5/2256 348/211.99 |
| 2010/0100081 A1* | 4/2010 | Tuma ..................... A61B 34/20 606/1 |
| 2011/0208093 A1 | 8/2011 | Gross et al. |
| 2011/0254922 A1* | 10/2011 | Schaerer ............ A61B 19/5244 348/46 |
| 2011/0263971 A1* | 10/2011 | Nikou ..................... A61B 90/39 600/424 |
| 2012/0046536 A1* | 2/2012 | Cheung .................. A61C 1/082 600/407 |
| 2014/0247336 A1 | 9/2014 | Vilsmeier et al. |

OTHER PUBLICATIONS

International Preliminary Report on Patentability, PCT/EP2011/067935, dated Apr. 15, 2014, pp. 1-7, The International Bureau of WIPO, Switzerland.

Decision to grant a European patent pursuant to ARticle 97 (1) EPC, European patent application No. 11769880.3. Notice from EPO dated Jun. 8, 2014; EP patent No. EP2765946; pp. 1-44, European Patent Office, Netherlands.

International Search Report for International Application No. PCT/EP2011/067935 dated Jun. 19, 2012 pp. 1-3.

\* cited by examiner

MEDICAL TRACKING SYSTEM COMPRISING MULTI-FUNCTIONAL SENSOR DEVICE

RELATED APPLICATION DATA

This application is a national phase application of International Application No. PCT/EP/2011/067935 filed Oct. 13, 2011 and published in the English language.

The present invention relates to a medical tracking system comprising at least one multi-functional sensor device which can be used as both a marker device and/or a marker detector device. The present invention further relates to a method for medical tracking using such a medical tracking system.

For many years, medical tracking or navigation systems are in use which are based on a tracking device which detects the position of markers which are attached to objects to be tracked. Typical systems comprise a 3D camera which captures images of dedicated marker devices. With the present invention, the strict division into marker devices and marker device detectors is broken by using a sensor device which can act as a marker device as well as a marker detection device.

This is achieved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The medical tracking system according to the present invention comprises at least one sensor device which can be positioned in a fixed position relative to a target. The sensor device comprises a marker device and a marker device detector. The marker device detector is capable of obtaining information for determining a relative position between the marker device detector and another marker device. This information may be sufficient to determine the relative position or it may be necessary to supplement this information by further information. The other marker device is a marker device other than the one comprised in the sensor device.

In this document, a target can be medical instrument such as a cutting block or a pointer, a part of an operation room equipment such as an operation room table or tripod or an anatomical structure such as a bone. If a sensor device is rigidly attached to a medical instrument and the medical instrument is rigidly attached to an anatomical structure, this means that the sensor device is automatically in a fixed position relative to the anatomical structure.

A fixed position in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other as explained below. A fixed position can for example be achieved by rigidly attaching one object to another. The term "position" in this document means a spatial location in up to three (in particular less than three) translational dimensions and/or an alignment in up to three (in particular less than three) rotational dimensions. The position can thus comprise up to six dimensions, wherein there is a parameter for each dimension. Depending on the application or workflow, the parameters of less than six dimensions may be required or desired. The spatial location can in particular be described just by a distance (between two objects) or just by the direction of a vector (which links two objects). The alignment can in particular be described by just the relative angle of orientation (between the two objects).

A marker device can for example be one or more (individual) markers in a predetermined spatial relationship. A marker device comprises one, two, three or more markers in a predetermined spatial relationship. This predetermined spatial relationship is in particular known to the tracking system and for example stored in a control unit of the tracking system.

It is the function of a marker to be detected by a marker detection device (for example, a camera or an ultrasound receiver), such that its spatial position (i.e. its spatial location and/or alignment) can be ascertained or information used for ascertaining its spatial position is provided, while the information provided by a single marker detection device might not be sufficient to ascertain all parameters which define the spatial position. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

The marker device detector is either just a sensor which outputs sensor data which are then analyzed by a processing unit in order to determine the position of a marker device or includes the processing unit, such that the marker device detector directly outputs the position of a marker device.

The medical tracking system further comprises a control unit configured to process a medical navigation workflow, which consists of two or more workflow steps, and to select the function of the sensor device as either acting as a marker device detector or as a marker device in a step of the medical navigation workflow. The control unit is preferably further configured to determine the relative position between the other marker device and the marker device detector from the information output by the marker device detector.

With such a sensor device, the number of instruments needed to perform the medical navigation workflow can be reduced, which means that less instruments have to be provided and sterilized. In addition, processing of the medical navigation workflow is accelerated because less instruments have to be handled, which means that the used instruments have to be changed less often.

In this document, "either acting as a marker device detector or as a marker device" means that the sensor device has the function of either a marker device detector means or a marker device means. The term "acting" thus has the meaning of "behaving as".

In a preferred embodiment, the sensor device comprises display for displaying at least a part of the marker device. In particular, one or more markers are displayed on the display. The displayed markers may supplement static markers on the sensor device.

Preferably, the markers making up the marker device are optical markers, which means that the marker device is an optical marker device, and the marker device detector is a still or video camera, and in particular a 2D camera. The camera captures an image of the optical marker device and calculates the position of the optical marker device. This is done by analyzing the configuration, shapes and sizes of the markers in the camera image.

In one embodiment, the optical marker device comprises a plurality of squares in a known configuration. Further preferably, each of the squares has one of at least two different sizes. Yet further preferably, the squares are arranged in different planes, which are preferably parallel to each other.

In a preferred embodiment, the tracking system comprises at least two sensor devices, wherein, in a particular step of the medical navigation workflow, one sensor device acts as a marker device and another sensor device acts as a marker device detector. In particular, the function of the two sensor devices changes between the two steps of the medical navigation workflow. This is particularly useful if, in one step of the workflow, a marker device has to be rigidly attached to a target, while in the next workflow step a marker device detector has to be attached to the target, or vice versa. The subsequent attachment of two different devices (a marker device and a marker device detector) can be replaced by switching between the two different functions of the same sensor device.

In one embodiment of the present invention, one of the sensor devices is positioned in a fixed position relative to a target and another sensor device acts as a pointer. This is particularly useful if an object, such as the target to which the sensor device is positioned in a fixed relative position, is to be registered and the sensor device acting as a pointer is used for registration.

A pointer is a rod which comprises a marker device fastened to it and can be used to measure off individual co-ordinates, in particular spatial co-ordinates (i.e. three-dimensional co-ordinates), on a part of the body, wherein a user guides the pointer (in particular, a part of the pointer which has a defined and advantageously fixed location with respect to the marker device attached to the pointer) to the position corresponding to the co-ordinates, such that the position of the pointer can be determined by using the tracking system to detect the marker device of the pointer. The relative location between the marker device of the pointer and the part of the pointer used to measure off co-ordinates (in particular, the tip of the pointer) is in particular known.

According to another embodiment, a sensor device further comprises an orientation sensor. This orientation sensor outputs orientation sensor data which represents the orientation of the sensor, and therefore of the sensor device, in up to three rotational dimensions. The reference system in which the orientation sensor data is determined is preferably an absolute, stationary reference system, such as ground-based reference system utilizing the direction of gravity.

If the sensor device comprising an orientation sensor is acting as a marker device, then it preferably transmits the orientation sensor data to a sensor device acting as a marker detection device or to the control unit of the medical tracking system. In this case, the detection of the position of the sensor device acting as a marker device can be supplemented by the orientation sensor data, thus making the detection result more reliable.

If the sensor device comprising an orientation sensor is acting as a marker detection device, then the orientation sensor data can be used to calculate the position of the detected marker device in an absolute reference system known to the sensor device acting as a marker detection device.

It is possible to use an off-the-shelf (consumer) device as a sensor device, such as an iPod touch or an iPhone provided by Apple Inc.

The present invention further relates to a method of medical tracking for supporting a medical navigation workflow. The method comprises the step of using a sensor device comprising a marker device and a marker device detector as a marker device detector in one step of the medical navigation workflow for obtaining information for determining the position of a marker device and using the same sensor device as a marker device in another step of the medical navigation workflow. The sensor device thus has a double functionality, wherein the appropriate functionality is chosen depending on the requirements of a particular step of the medical navigation workflow. The functionality is preferably chosen by a control unit which processes the medical navigation workflow.

In one embodiment, the method utilizes two sensor devices, one of the sensor devices acting as a marker device of a pointer for pointing at sample points and another one of the sensor devices, being positioned in a fixed position relative to a target, acting as a marker device detector for obtaining information for determining the position of the marker device. In this embodiment, a first sensor device acting as a marker detection device is preferably rigidly attached to an anatomical structure such as a bone or to a medical instrument such as a cutting block, which in turn can be rigidly attached to an anatomical structure. A second sensor device acting as a marker device is preferably rigidly attached to a pointer, wherein the second sensor device has a known relative position to the pointer, in particular to the tip of the pointer. When the first sensor device detects the position of the second sensor device, then the position of the tip of the pointer in a reference system of the first sensor device can be calculated, such that points indicated by the tip of the pointer can be sampled. Preferably, the method comprises the step of registering the target by sampling a plurality of sample points, which preferably lie on the surface of the target.

In another embodiment of the present invention, the sensor device acting as a marker device and the sensor device acting as a marker device detector both comprise an orientation sensor and the orientation sensor data are used when the position of a marker device is determined The orientation sensors preferably generate orientation sensor data in an absolute reference system as explained above. This means that the position of the marker device can be determined from the two sets of orientation sensor data as well as from the information output by the marker device detector. The two determined positions can be combined, for example for increasing the accuracy of the determined position or for validating one of the determined positions with the other one of the determined positions.

In one embodiment of the present invention, the marker detector is a camera and the sensor device further comprises a display device and is positioned in a fixed position relative to a bone, wherein the image captured by the camera is displayed on the display device and a characteristic property of the bone can be acquired based on the camera image on the display device. This enables to acquire the characteristic property into a sensor device which is attached to the bone, such that the relation between the inputted characteristic property and the bone is immediately given. The characteristic property is acquired either by being inputted manually or by being detected automatically. The characteristic property can for example be an anatomic direction of the bone, such as the anteroposterior, dorsoventral or lateral axis.

The additional feature of this embodiment, that is acquiring a characteristic property of a bone to which a sensor device comprising a display and a camera is attached based on a camera image showing at least a part of the bone or an anatomical structure, such as a foot or a hand, attached to the bone, can also be utilized apart from this invention as a stand-alone invention or in combination with other inventions.

In one variant of this embodiment, an information which is overlaid over the camera image is manipulated by using an input device of the sensor device, such as a button, a dial or a touch functionality of the display. This information is preferably an arrow which can be aligned on the camera image by using the input device.

In another variant of this embodiment, the characteristic property of the bone is acquired automatically, for example by an automatic analysis of the camera image.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

Figure 2:
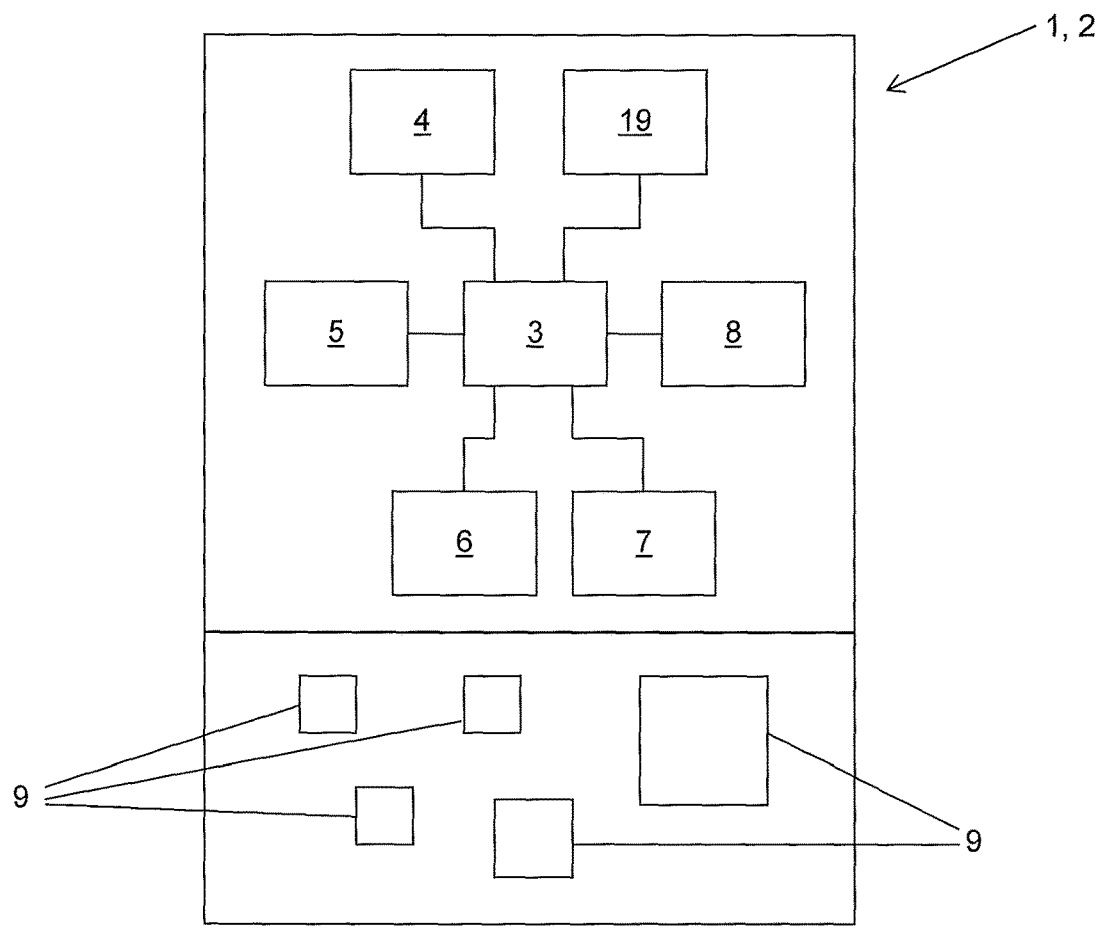

The present invention shall be explained in more detail with reference to the accompanying drawings. The figures show:

FIG. 1 a schematic structure of a medical tracking system,

FIG. 2 a schematic structure of a sensor device,

FIGS. 3 to 12 visualizations of steps of first medical navigation workflow, and

FIGS. 13 to 16 visualizations of steps of a second medical navigation workflow.

FIG. 1 schematically shows a medical tracking system, also referred to as a medical navigation system, comprising two sensor devices 1 and 2. The structure of the sensor devices 1 and 2 is shown schematically in FIG. 2.

In this exemplary example, a sensor device 1, 2 comprises a processor or central processing unit (CPU) 3 which is connected to a display 4, the gyroscope 5, two cameras 6 and 7 and a Bluetooth transceiver 8. The 2D-cameras 6 and 7 are located on opposite sides of a housing of the sensor device 1, 2. Preferably, camera 6 is located on the same side as the display 4. The cameras 6 and 7 act as position sensors. A sensor device 1,2 further comprises an optional distance sensor 19.

The gyroscope 5 is configured to determine orientation data which represent the orientation of the sensor device 1, 2 in three rotational dimensions in an absolute, ground-fixed reference system based on the direction of gravity. The gyroscope 5 acts as an orientation sensor. The processor 3 acts as control unit. This means that both sensor devices 1, 2 comprise a control unit.

At least one of the sensor devices 1, 2 comprises optical markers 9, which in the present case are rectangles or squares. The markers 9 have the same size and are arranged in a known pattern. This pattern is preferably three-dimensional, which means that the markers 9 are preferably arranged in two or more (parallel) planes. The sizes of some or all of the markers 9 can also be different. The shape of a sensor device can also be used as a marker.

FIGS. 3 to 12 show different steps of a first medical navigation workflow. In the exemplary application of the first workflow, the properties of a knee joint between a femur F and a tibia T are determined.

Figure 3:
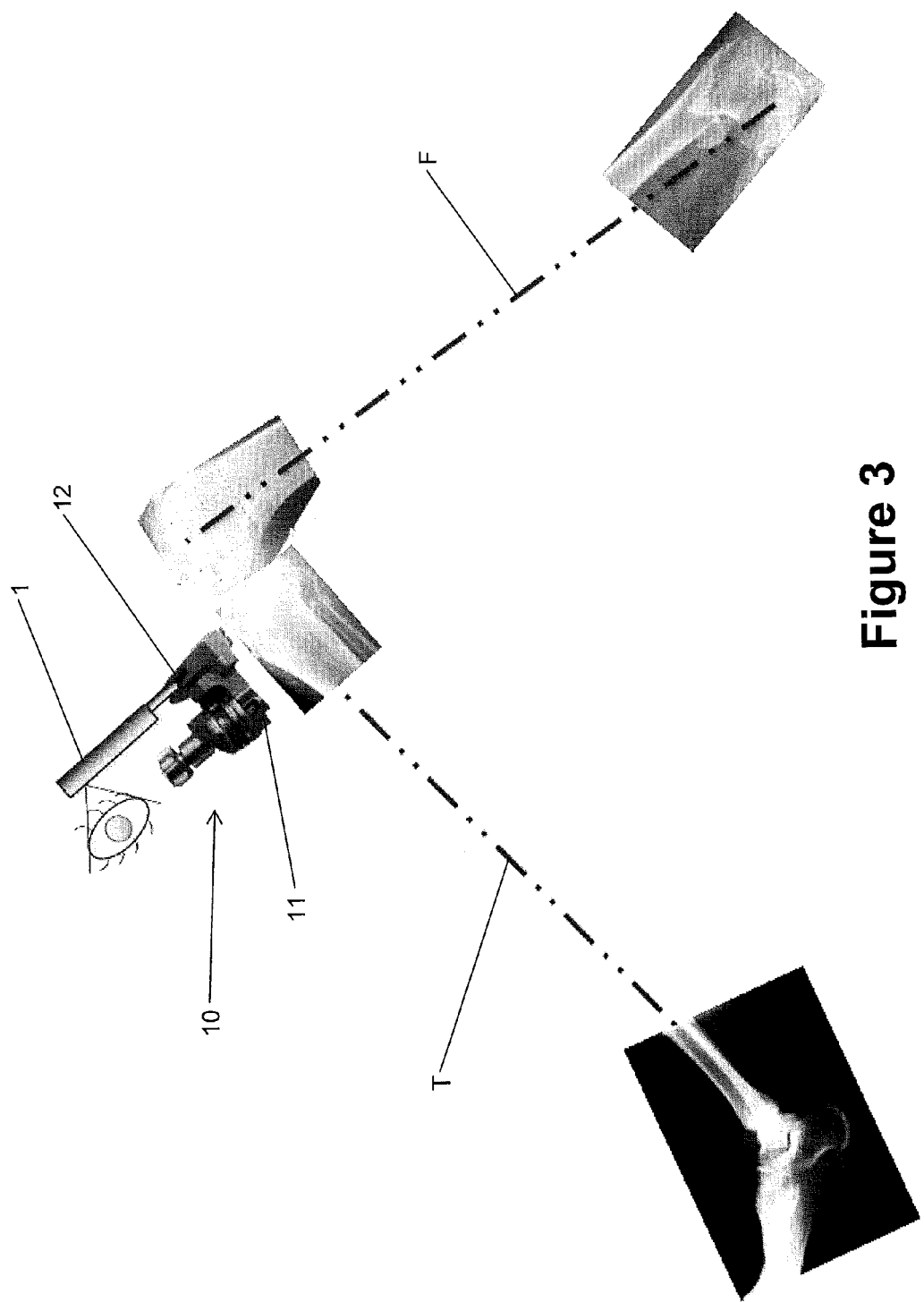

In the step shown in FIG. 3, an adjustable cutting block 10 is attached to the tibia T. The adjustable cutting block 10 comprises a base 11 and an adjustable cutting slot 12 which is adjustable relative to the base 11. The first sensor device 1 is rigidly attached to the cutting slot 12 of the cutting block 10 in a reproducible position relative to the slot 12. The field of view of the camera 7 is indicated schematically by the eye symbol.

Figure 4:
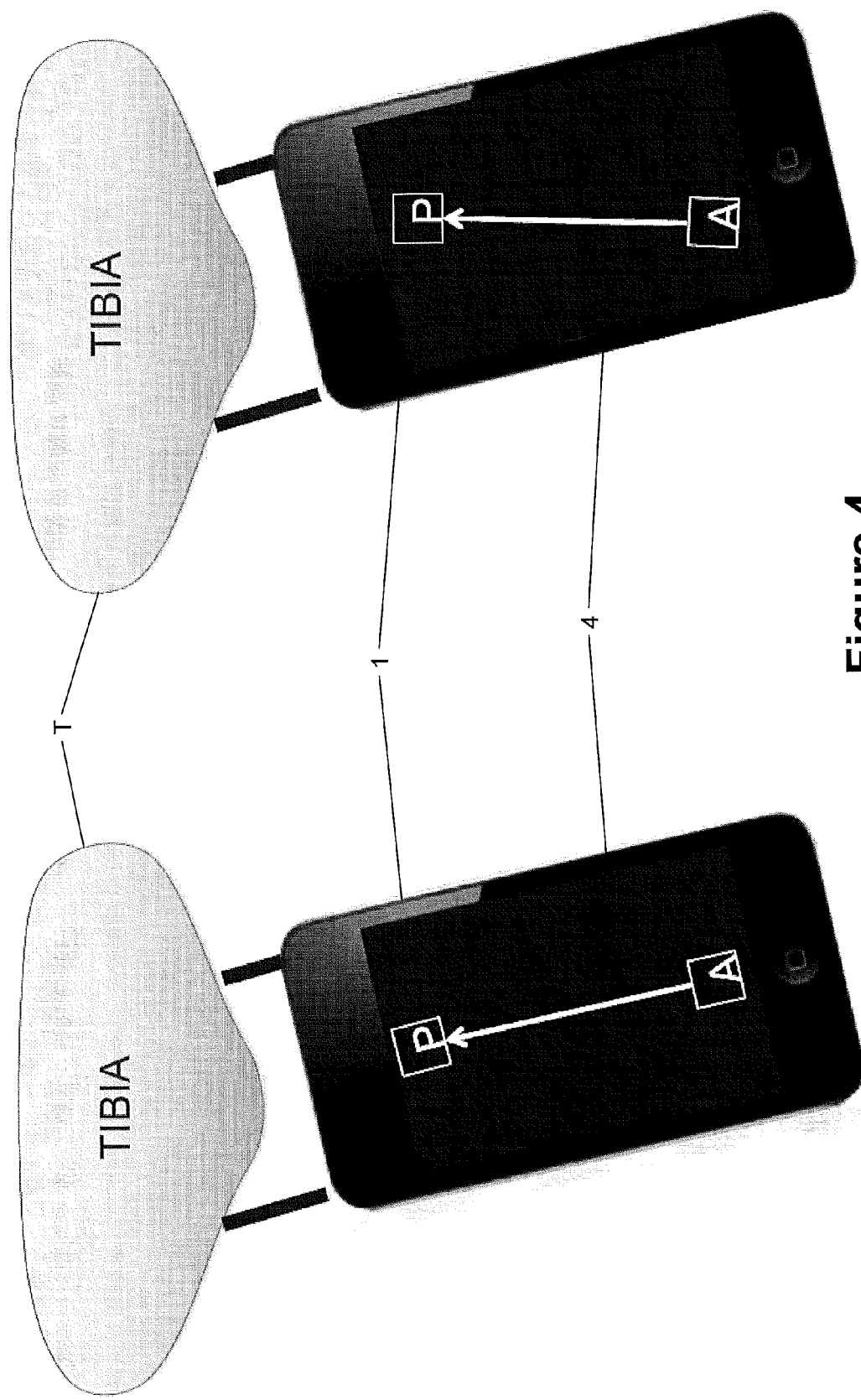

In the workflow step shown in FIG. 4, the sensor device 1 acquires the anterioposterior (AP) axis or direction as a property of the tibia T. The AP direction can be determined automatically, for example if the patient is lying flat on his back. In this case, the AP direction can be acquired as being parallel or in a known relation to gravity.

In the implementation shown in FIG. 4, the AP direction is acquired based on manually inputted AP data. In this case, an arrow virtually representing the AP direction is displayed on the display 4. A user can then input data to align the AP arrow shown on the display 4 with the actual AP direction of the tibia T. For this purpose, the AP arrow can be rotated in the display plane, for example by using buttons (not shown) of the sensor device 1 or by touching the display 4 if the display 4 is a touch sensitive display.

As a preferred option, the AP arrow is overlaid on an image captured by the camera 7 which is located in the housing of the sensor device 1 on an opposite side of the display 4. This image typically shows a part of the tibia, and preferably also a part of the foot. This overlay leads to an improved accuracy of the manually inputted AP direction. In addition or as an alternative, the AP direction can be automatically determined from an image analysis performed by the CPU 3.

In general, any property of an anatomical structure can be acquired by manipulating information, such as an arrow, displayed on the display of a sensor device.

In the workflow steps shown in FIGS. 5 and 6, the second sensor device 2, which comprises markers 9 as explained with reference to FIG. 2, is rigidly attached to a pointer 13. The relative position between the markers 9 and the tip of the pointer 13 is known. Additional markers, such as the circles 14, can be displayed on the display 4 of the sensor device 2. In this workflow step, the second sensor device 2 acts as a marker device and the first sensor device 1 acts as a marker device detector. In a modification of this example, there are no fixed markers 9, but only markers 14 displayed on the display 4.

The pointer 13 comprises an adaptor for accommodating a sensor device 1 or 2 in an unambiguous, reproducible position relative to its tip. Some or all of the fixed markers 9 may be located on the pointer 13.

In the medical workflow, landmarks of the tibia T are sampled by touching the landmark with the tip of the pointer 13 and determining the position of the markers 9 and 14. Due to the known constellation of the markers relative to the tip of the pointer 13, the position of the tip can be determined from the position of the markers. The positions of the markers are determined by the sensor device 1. The camera 7 of the sensor device 1 captures an image comprising the markers. Due to the known constellation and sizes of the markers, the CPU 3 of the sensor device 1 can analyze the output image of the camera 7 in order to detect the markers and hence the positions of the landmarks in a reference system of the sensor device 1. The CPU 3 uses the size, the shape and the relative positions of the markers in the output image of the camera to determine the position of the tip of the pointer. The position of the markers may be more accurate by using the distance sensor 19, such as a laser beam generator, to calculate the distance of the markers from the sensor device.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Other landmarks include a landmark defined by the rim of the acetabulum, for instance by the centre of the rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur head when moved relative to the acetabulum.

A detection point is in particular a point on the surface of the anatomical structure which is detected, for example by a pointer.

Figure 5:
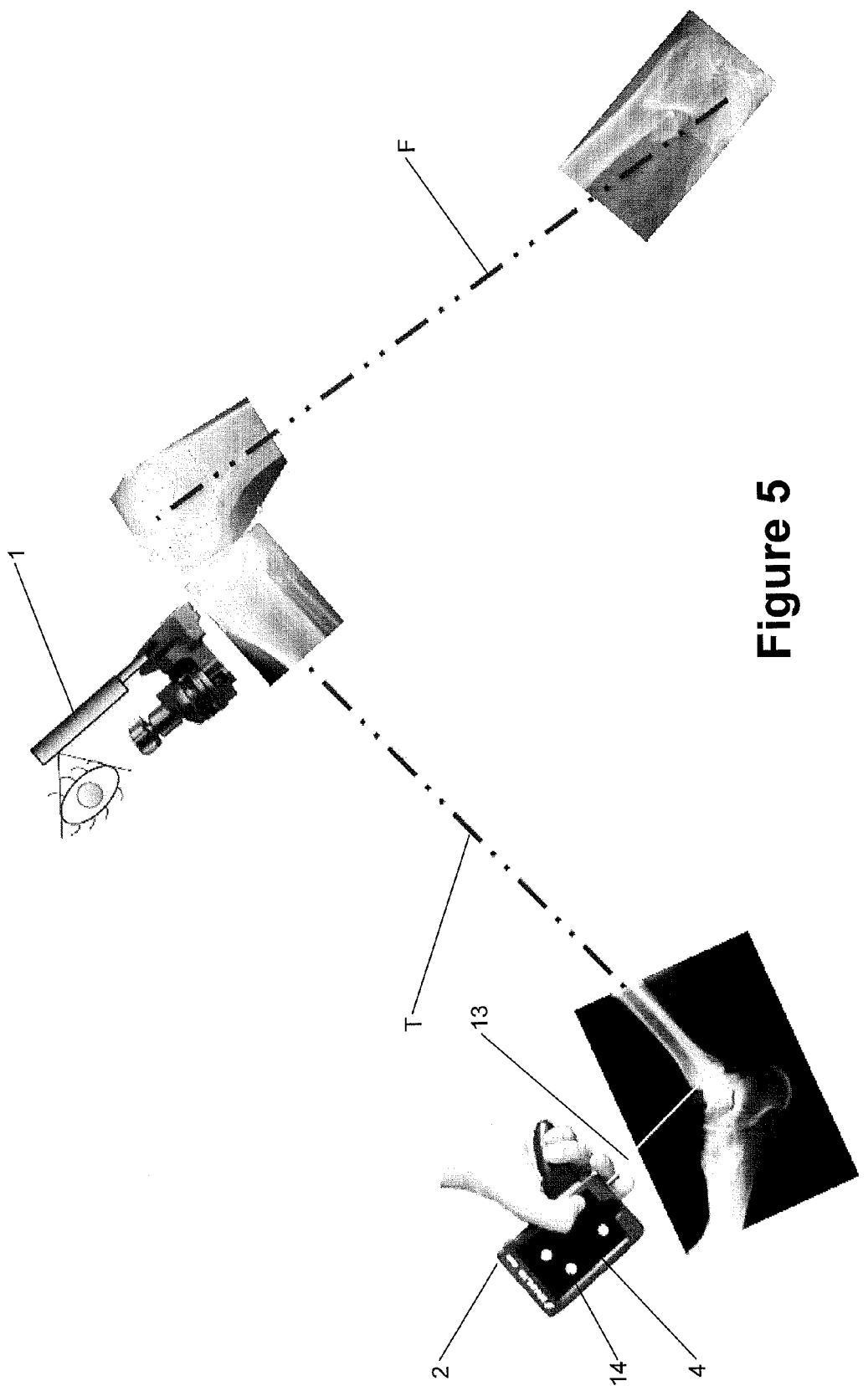

In the workflow step shown in FIG. 5, the lateral and medial malleolus landmarks are determined. In the workflow step shown in FIG. 6, the proximal endpoint of the tibia mechanical axis is sampled. With the sampled landmarks and the acquired AP direction, the tibia T is now registered relative to the sensor device 1. For the workflow step shown in FIG. 6, the sensor device 1 switches to the other camera 6, which captures a volume different from the volume captured by camera 7.

With the tibia T being registered, the mechanical axis of the tibia T is known. The reference system of the sensor device 1 is in a known relation to the cutting slot 12. As long as the adjustment of the cutting slot 12 is not changed compared to the base 11, then the registration is also known with the base 11 as a reference.

In the next workflow steps, the femur F is registered. In the workflow step shown in FIG. 7, the sensor device 2 is rigidly attached to an adjustable cutting block 15. A cutting block 15 comprises a base 16 which is rigidly attached to the femur F and a cutting slot 17 which is adjustable relative to the base 16. The sensor device 1 is attached to the cutting slot 17.

Figure 8:
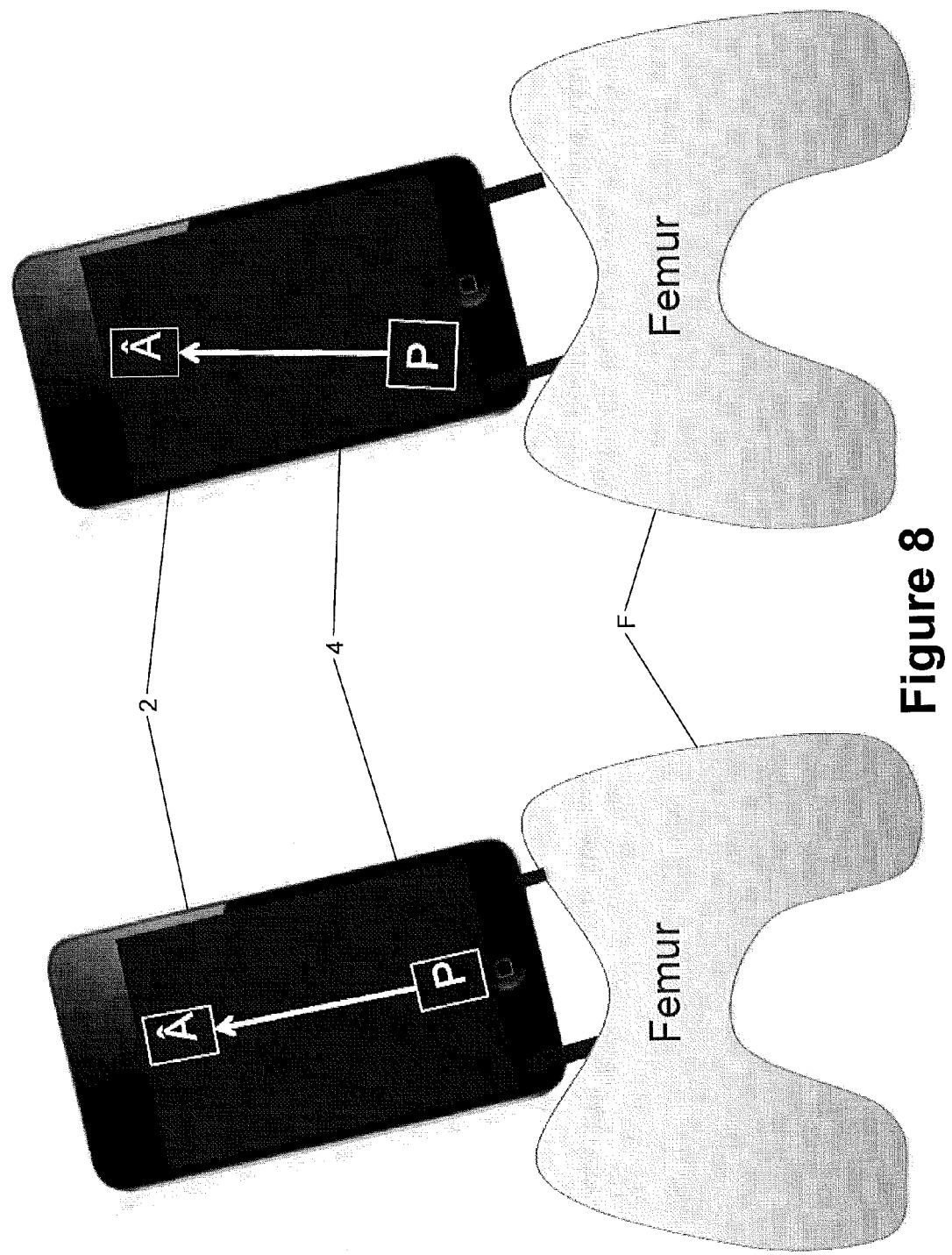

In the workflow step shown in FIG. 8, the AP direction of the femur is acquired. The possibilities for acquiring the AP direction of the femur F are analog to the possibilities described for the tibia with reference to FIG. 4, such that a detailed explanation is omitted.

Figure 9:
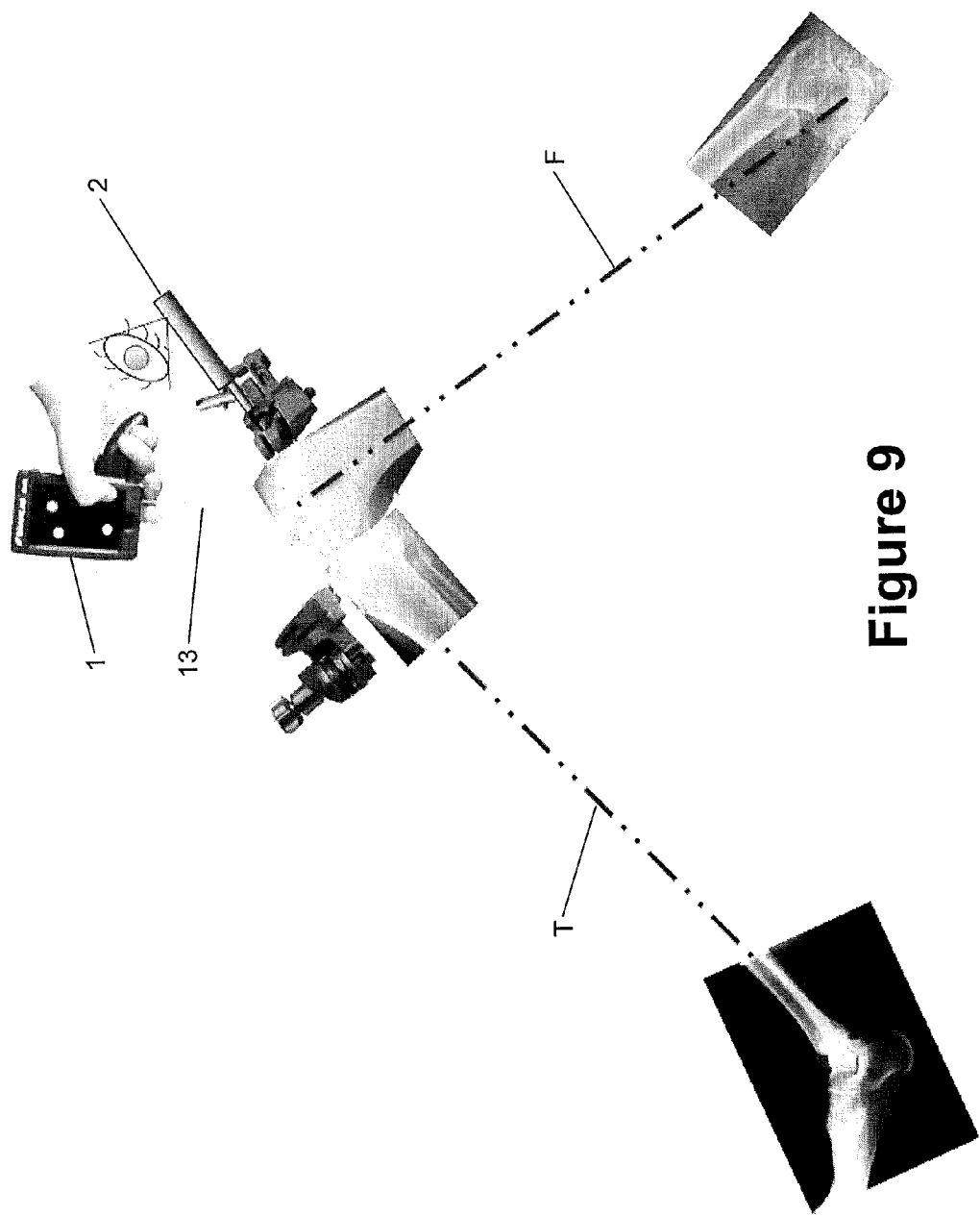

In the workflow step shown in FIG. 9, the sensor device 1 is used in combination with the pointer 13 to sample the distal end point of the femoral axis.

Figure 10:
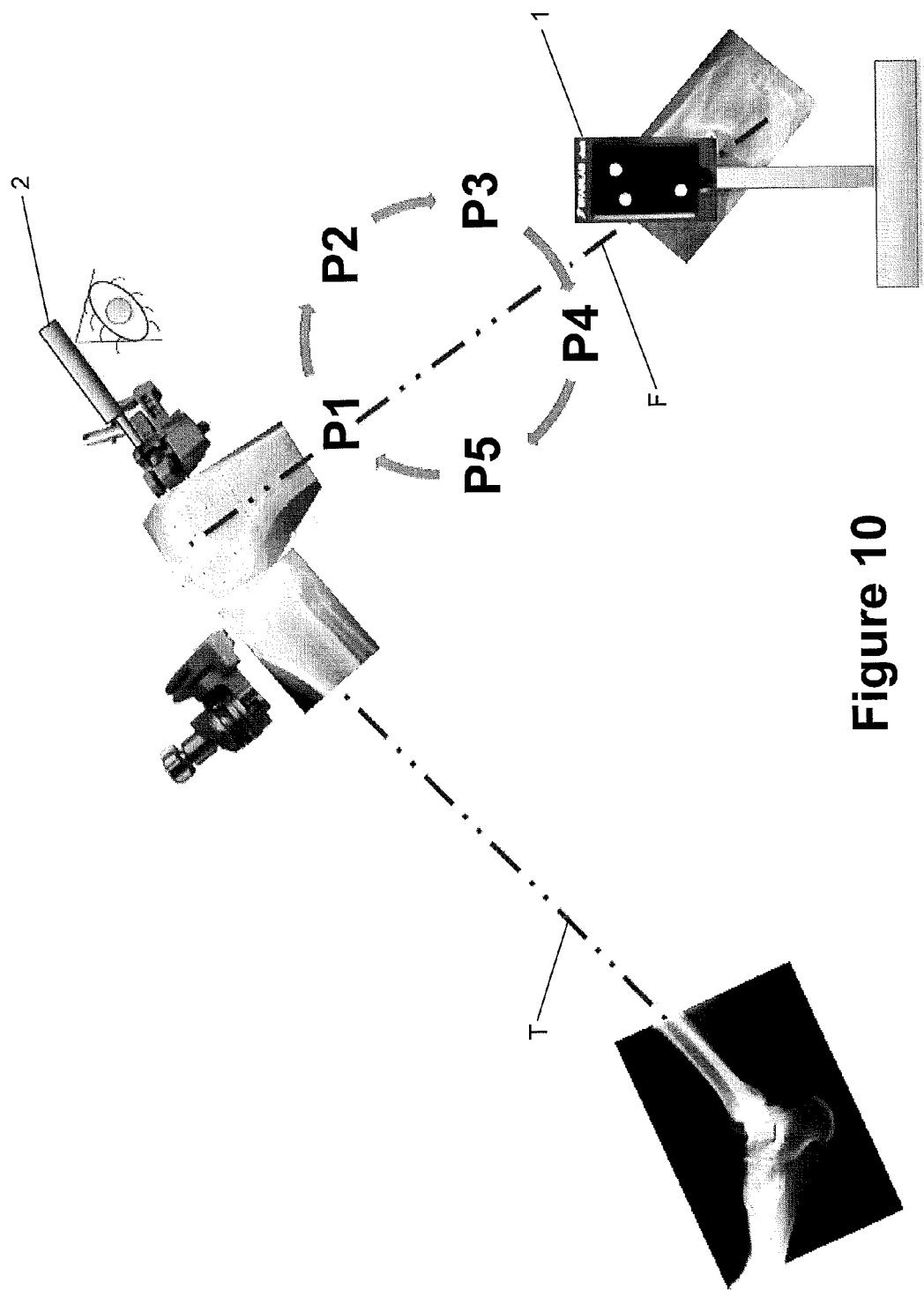

In the workflow step shown in FIG. 10, the sensor device 1 is detached from the pointer 13 and rigidly fixed in an absolute position. For example, the sensor device 1 is rigidly attached to a tripod or an operation room table, in particular to a rail of the table. Then, the femur F is pivoted about its head. This means that the sensor device 2 moves on a spherical shell centered about the center of the femoral head. Using a camera 6 or 7, the CPU 3 of the sensor device 2 determines the relative position of the sensor device 2 by detecting the markers 9 and 14 of the sensor device 1 in analogy to the step described with reference to FIGS. 5, 6 and 9. From the plurality of relative positions P1 to P5 of the sensor device 2 relative to the sensor device 1 and the known fact that the sensor device 2 moves on spherical shell about a fixed center, this center, which is the center of the femoral head, can be calculated.

Now that the distal endpoint of the femoral axis, the center of the femoral head and the AP direction of the femur F are known, the femur F is registered in a reference system of the sensor device 2, which is in a fixed relation to a reference system of the cutting slot 17.

In the workflow steps shown in FIGS. 9 and 10, the first sensor device 1 acts as a marker device and the second sensor device 2 acts as a marker device detector. In general, the function of a sensor device 1 or 2, that is whether a sensor device acts as a marker device or a marker detector device, is selected by a CPU 3 based on the currently performed workflow step.

For the workflow step shown in FIG. 11, the first sensor device 1 is re-attached to the cutting slot 12 of the cutting block 10 in the same relative position to the cutting slot 12 as in the workflow steps explained with reference to FIGS. 3 to 6. This means that, as long as the cutting blocks 10 and 15 are not adjusted, the sensor device 1 is in a fixed relative and registered position to the tibia T and the sensor device 2 is in a fixed relative and registered position to the femur F.

Figure 11:
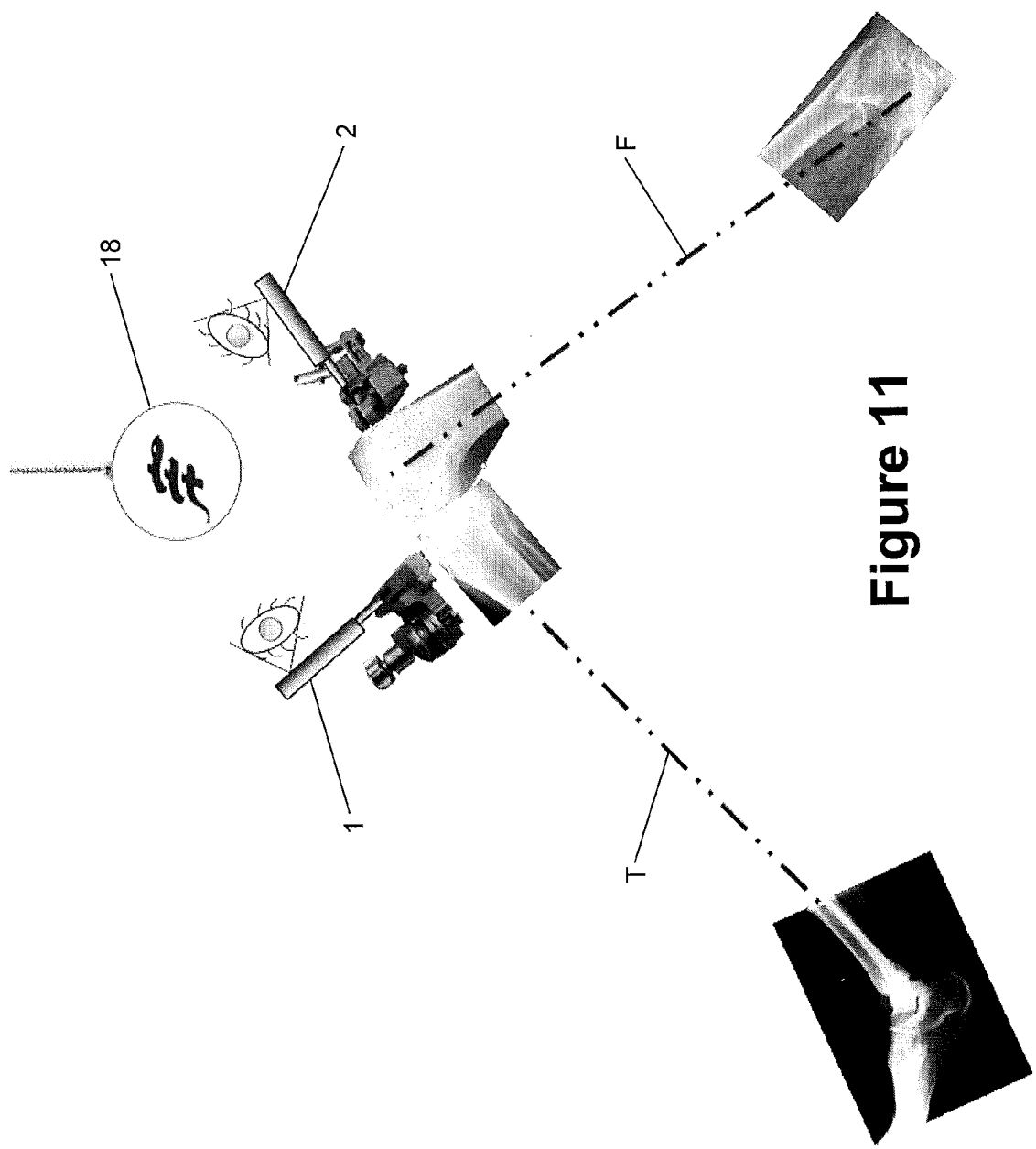

In the workflow step shown in FIG. 11, a measurement of the relative position between the two sensor devices 1 and 2 is performed, including the step of exchanging sensor data and using a reference. Exchanging means that at least one of the sensor devices transmits its sensor data, like the orientation data acquired by its gyroscope 5, to the other sensor device using the Bluetooth transceivers 8. Preferably, both sensor devices 1 and 2 exchange their respective orientation data, such that the CPUs 3 of both sensor devices 1 and 2 know the sensor data, like the orientation data, of both sensor devices. In this implementation, the gravity field of the earth acts as a reference for the synchronization.

In addition or as an alternative, a reference object 18 is used as a reference. In this implementation, the reference object 18 is imaged by at least one camera 6 or 7 of each sensor device 1 and 2. By image analysis, the relative position of the reference object 18 relative to the sensor devices 1 and 2 is calculated by the respective CPU 3. The position data representing the relative position of the reference object 18 to a sensor device is then transmitted to the other sensor device using the Bluetooth transceivers 7. In this implementation, again, the position information of (just) one sensor device can be transmitted to the other sensor device, or each sensor device can receive the position data from the other sensor device.

After measurement of the relative position, at least one of the sensor devices 1 or 2 knows the relative position, this means at least the relative orientation in three-rotational dimensions, of the other sensor device in its own reference system. The relative spatial location is not needed in the present workflow, but may also be determined Since the tibia T and the femur F are registered, the sensor device thus also knows the relative position of the femur F and the tibia T. Preferably, the registration data representing the relation of the bone and the sensor device is also transmitted to the other sensor device. This, again, is performed either in one direction only or both sensor devices transmit the registration data.

Figure 6:
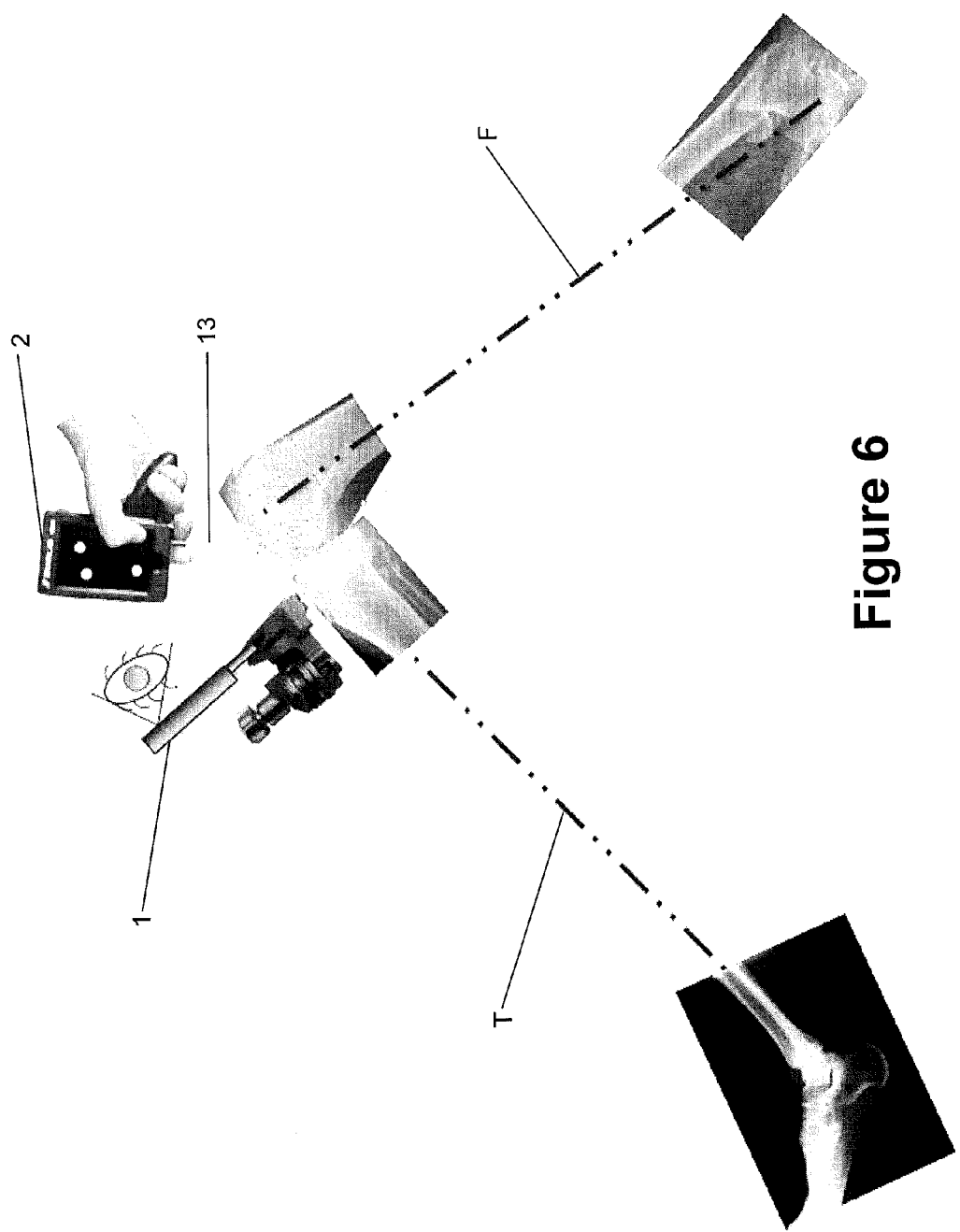
Figure 7:
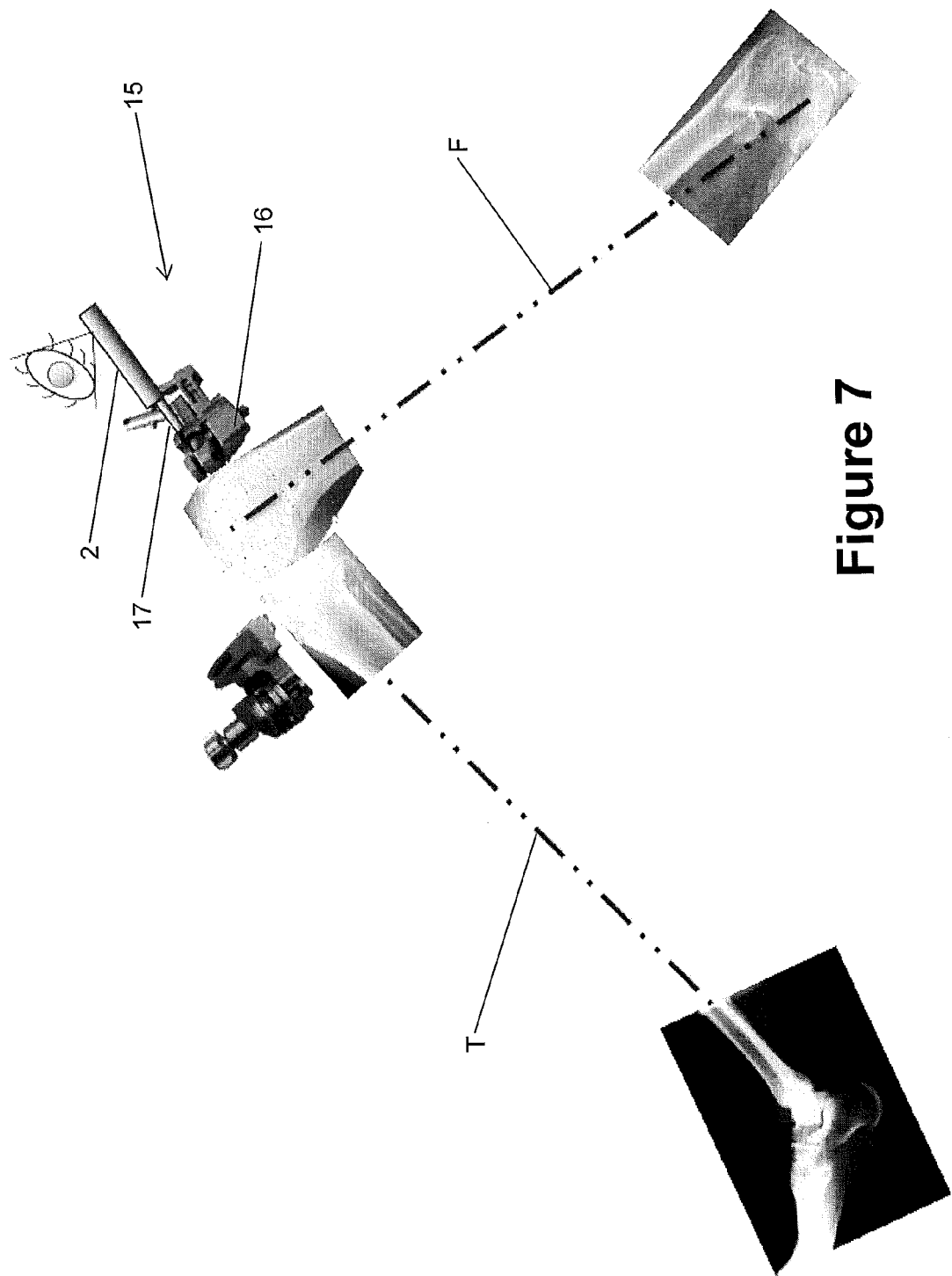

This approach for determining the relative position between the two sensor devices can also be used if one of the sensor devices is used as a marker device detector, such as in the workflow step shown in FIGS. 5 and 6, either replacing or supplementing the use of the markers.

Figure 12:
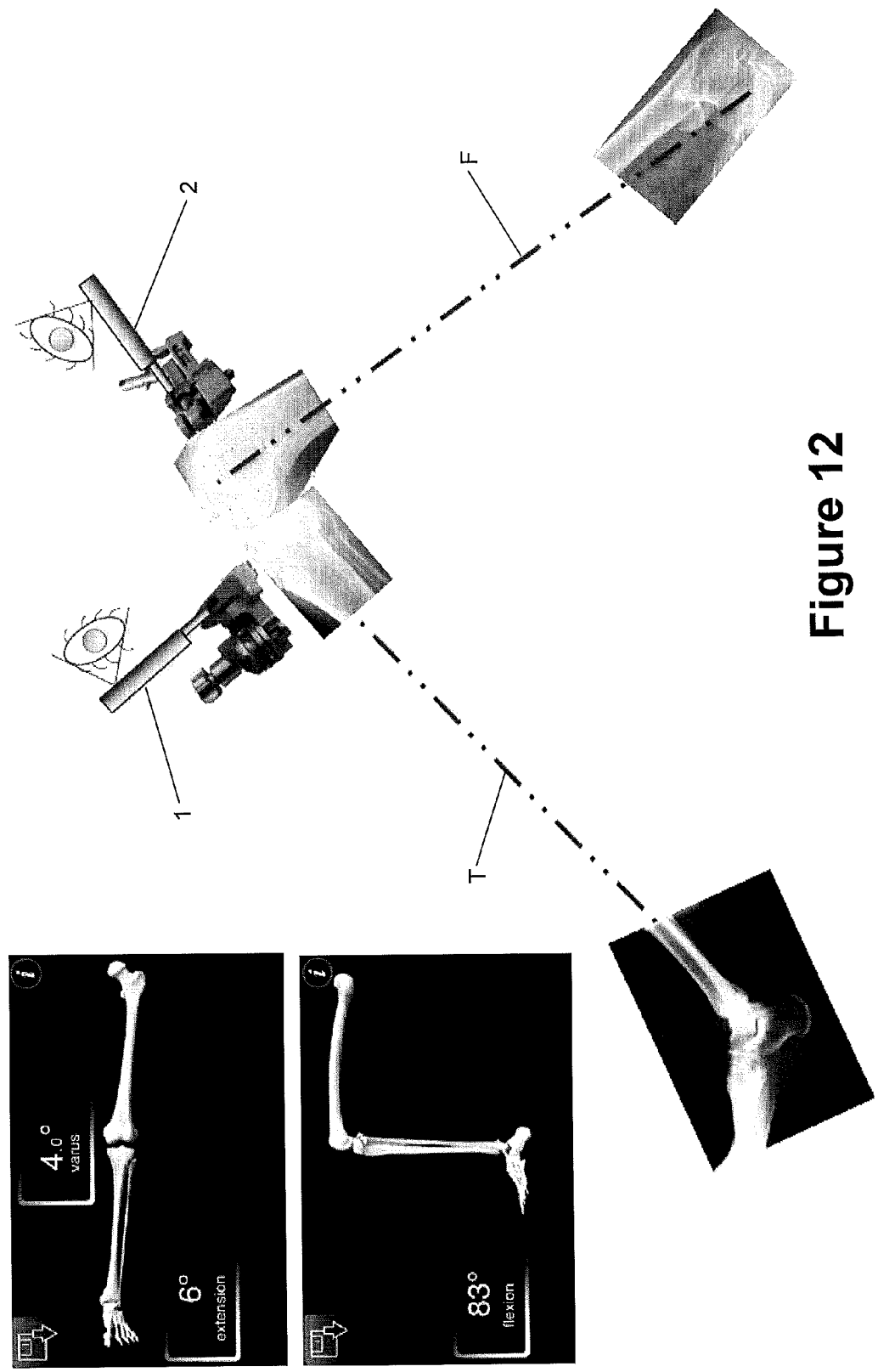

In the workflow step shown in FIG. 12, the tibia T is moved relative to the femur F using the knee joint. A measurement of the relative positions between the sensor devices 1 and 2 is performed in a plurality of positions. For each measurement, the sensor devices 1 and 2 exchange their orientation data and/or the position data of the reference object 18 such that at least one of the CPUs 3 can calculate the relative position of the sensor devices 1 and 2, and therefore of the femur F and the tibia T. If one measurement is taken in full extension and one measurement is taken in full flexion of the joint, then the range of motion of the knee joint can be determined From the relative position, also the varus or valgus angle can be determined. The values of the range of motion as well as the varus/valgus value may be shown on the display 4 of a sensor device, such as depicted in the screenshots in the upper left of FIG. 12.

FIGS. 13 to 16 show steps of a second medical workflow. These steps require the registration of the tibia T and the femur F as explained above with reference to FIGS. 4 to 6 and 8 to 10, with the same preconditions that an adjustable cutting block 10 is attached to the tibia T and an adjustable cutting block 15 is attached to the femur F. The positional relation between the sensor device 1 and the cutting slot 12 is known, as is the positional relation between the sensor device 2 and the cutting slot 17.

Figure 13:
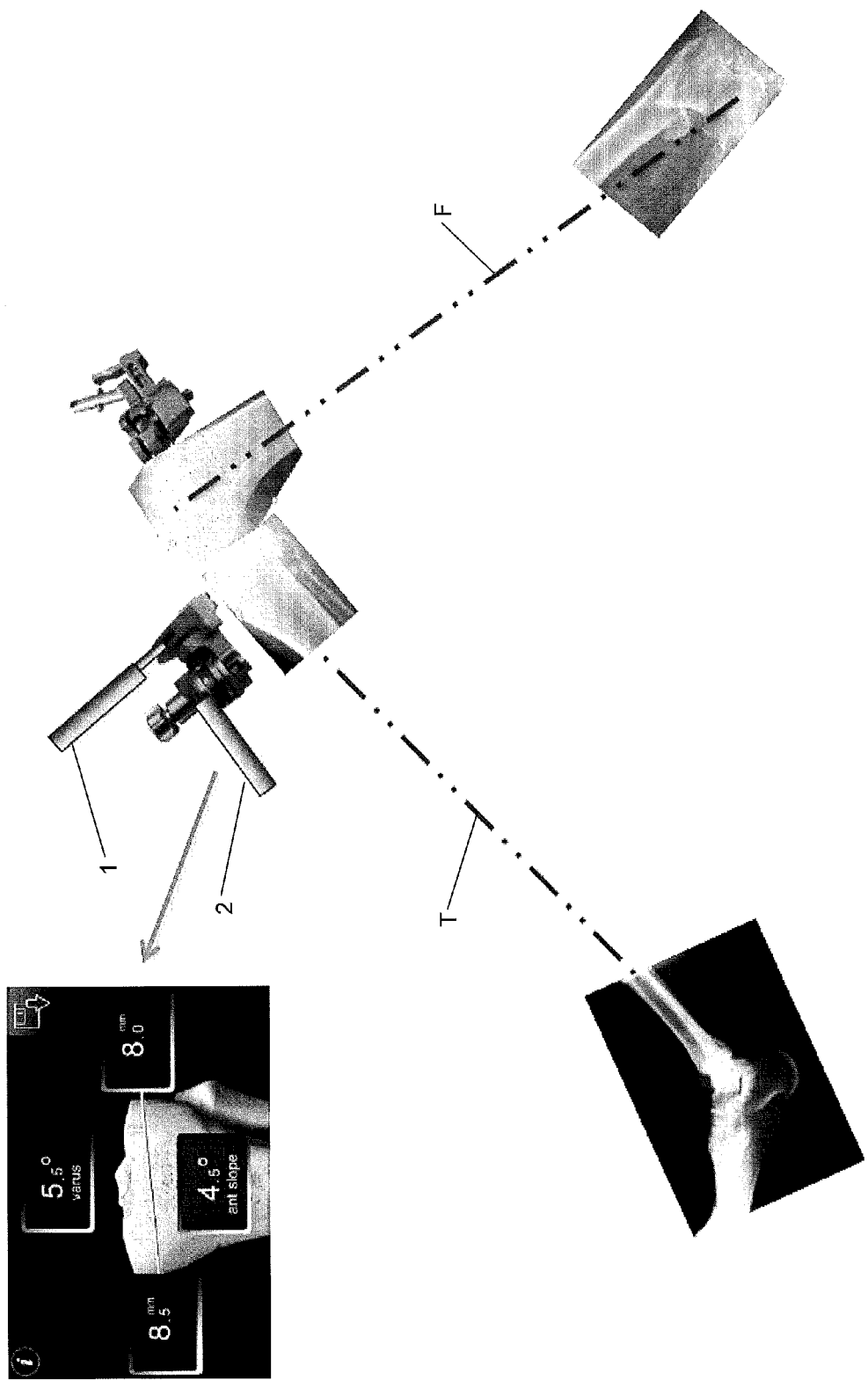

In the workflow step shown in FIG. 13, the sensor device 1 is rigidly attached to the cutting slot 12 and the sensor device 2 is rigidly attached to the base 11 of the cutting block 10. With the registration of the tibia T in the reference system of the sensor device 1, and the known relation between the sensor device 1 and the cutting slot 12, the current adjustment of the cutting slot 12 relative to the tibia T can be shown on the display 4 of any of the sensor devices as indicated in the screenshot shown in the upper left of FIG. 13.

A first measurement of the relative position between the sensor devices 1 and 2 is then performed as explained above with reference to FIG. 11. If the cutting block 10 is then adjusted, the relative position between the sensor devices 1 and 2 changes. By repeatedly measuring the relative position and calculating the current slot adjustment relative to the tibia T from the relative position, the cutting slot 12 can be adjusted to a desired setting. For example, one of the sensor devices 1 and 2 can output indication information if the current adjustment of the cutting slot 12 relative to the tibia T equals the desired setting. This indication information can be of optical, acoustical or tactile nature.

In this workflow step, the adjustment of the cutting block 10 is tracked using the sensor device 2 as a reference. If the sensor device 1 would use gravity as a reference, then any movement of the tibia T would impair the adjustment of the cutting slot 12. This is overcome by using the sensor device 2, which is rigidly attached to the tibia T via the base 11 of the cutting block 10, as a reference and performing measurements of the relative position by exchanging the orientation data and/or position data.

Figure 14:
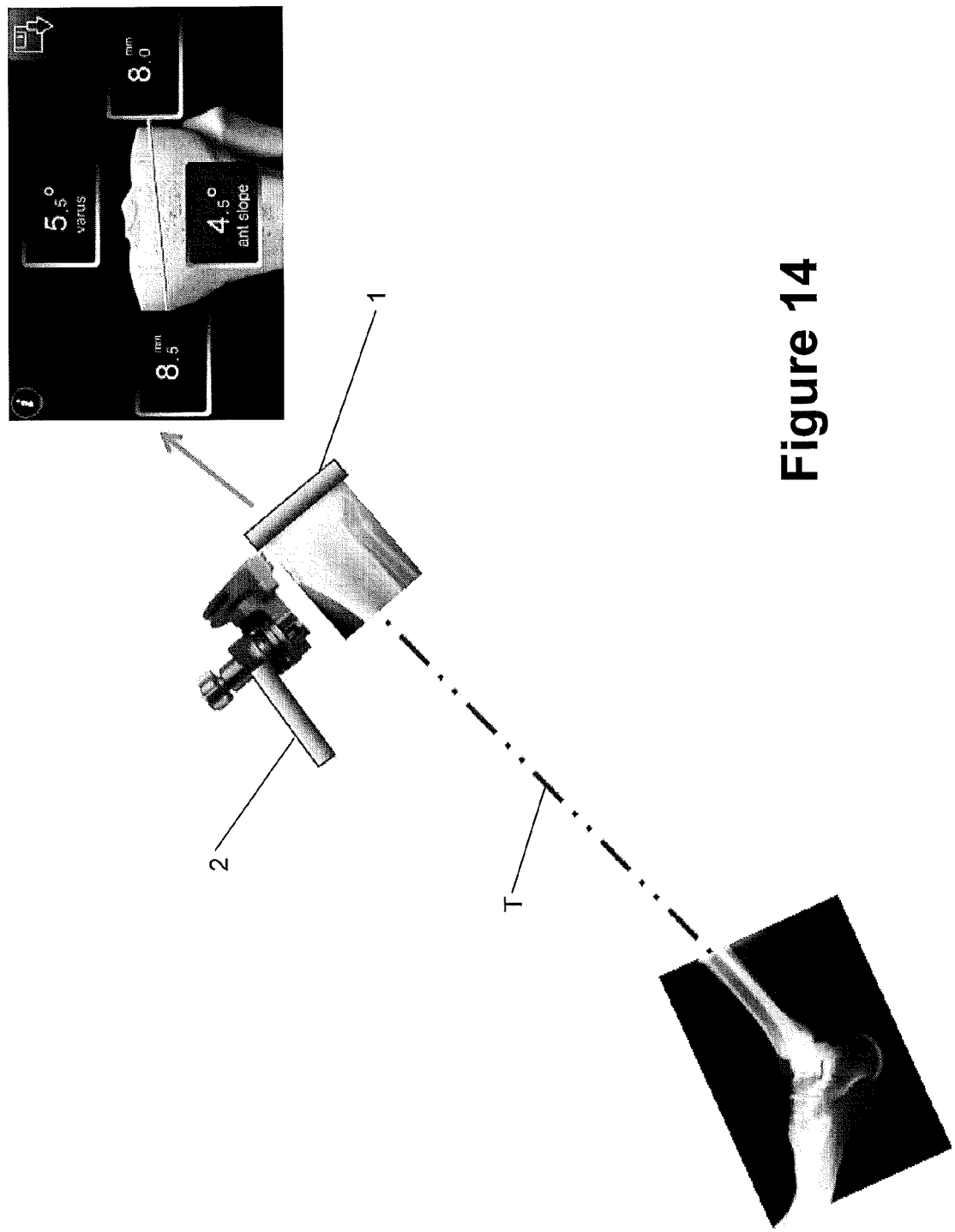

In the optional workflow step shown in FIG. 14, it is assumed that the cutting process of the tibia T has been performed. In this workflow step, a defined surface of the sensor device 1 is laid onto the cut surface of the tibia T. Then, a measurement of the relative position between the sensor devices 1 and 2 is performed. From this relative position, the position of the cut surface relative to the tibia T can be calculated for a verification step. As indicated in the screenshot in the upper right in FIG. 14, the actual position of the performed cut is displayed. By activating the disc symbol in the upper right of the screenshot, the actual position of the cut surface can be saved for documentation purposes.

Figure 15:
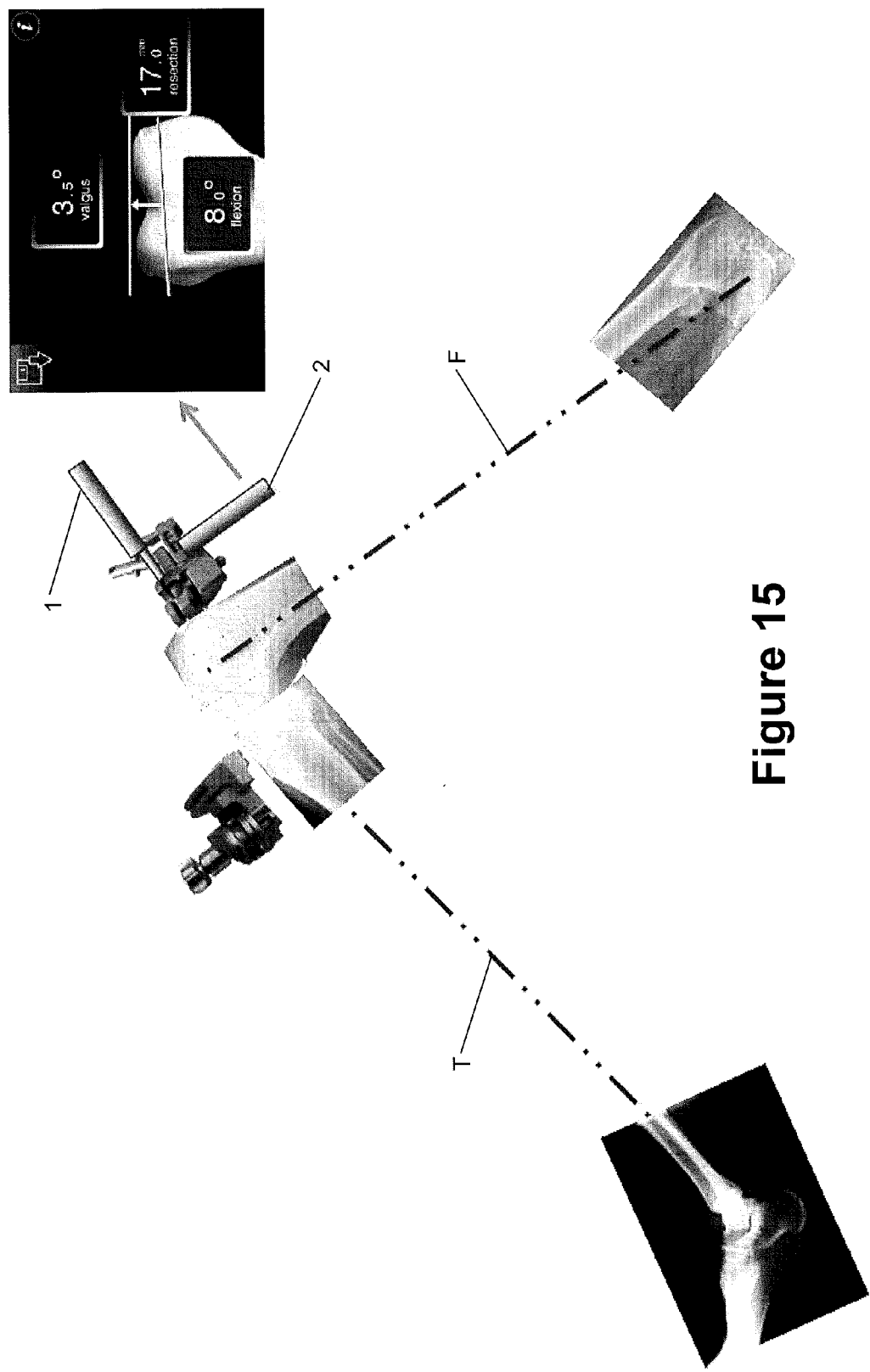

In the workflow step shown in FIG. 15, the cutting block 15 attached to the femur F is adjusted in analogy to the adjustment process of the cutting block 10 attached to the tibia T as described with reference to FIG. 13. However, for the adjustment of the cutting block 15, the sensor device 1 is rigidly attached to the base 16 and the sensor device 2 is rigidly attached to the cutting slot 17 of the cutting block 15.

Figure 16:
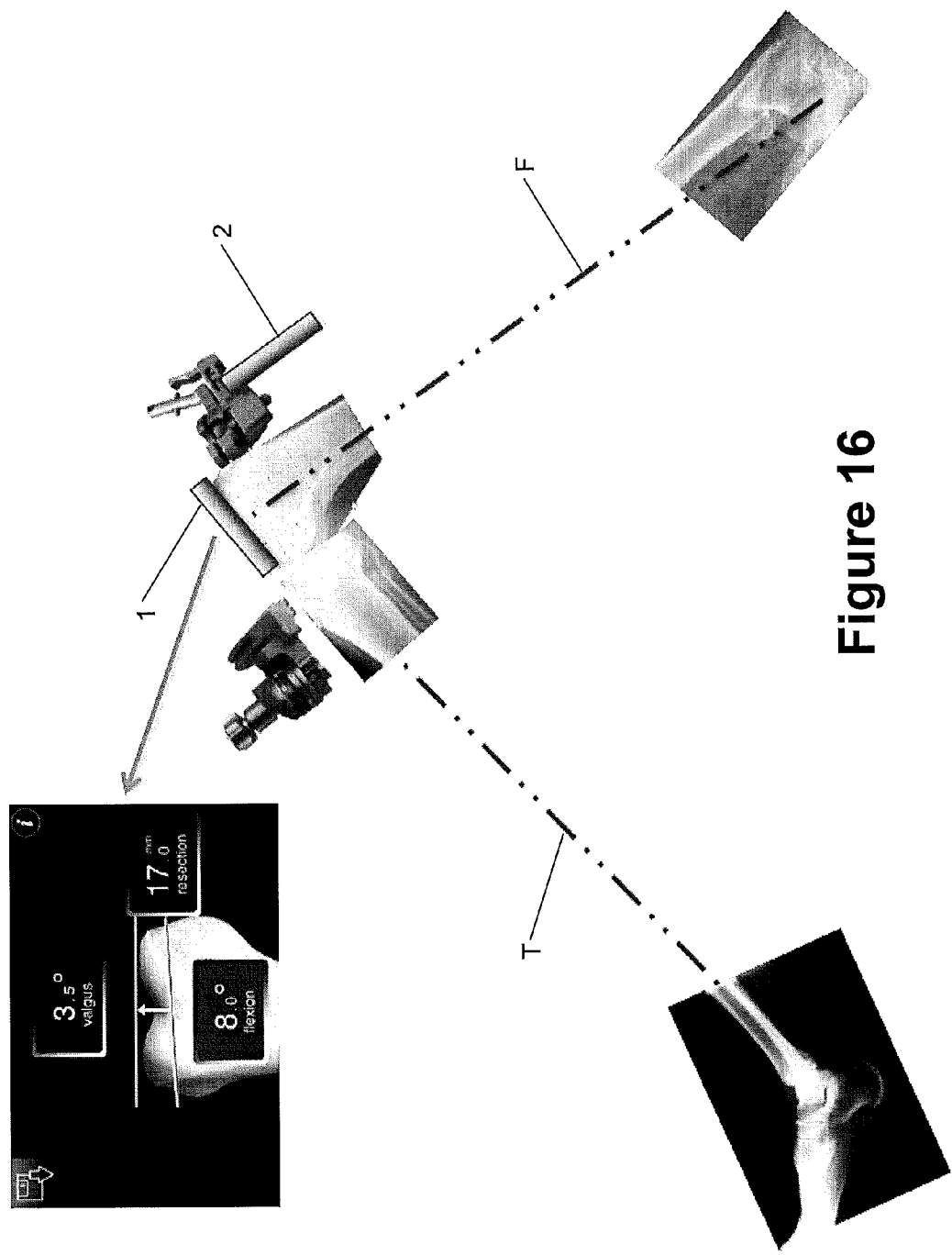

In the optional workflow step shown in FIG. 16, a defined surface of the sensor device 1 is laid onto the cut surface of the femur F. By measuring the relative position between the sensor devices 1 and 2, the cutting surface can be verified in analogy to the process described with reference to FIG. 14. Again, the actual position of the cut surface can be saved for documentation purposes by clicking on the disc symbol of the screenshot shown in the upper left of FIG. 16.

The desired setting of the cutting slot 12 or 17, respectively, can be calculated automatically based on a 3D image dataset representing a 3D image of the tibia or femur, respectively. In addition or as an alternative, the varus/valgus value and/or the range of motion acquired in the workflow step described with reference to FIG. 12 can be used for determining the desired setting.

When performing a medical workflow using the medical tracking system of this exemplary embodiment, the next step of the workflow is begun once the completion of the previous step is automatically detected or manually inputted. So the completion is typically known only to the sensor device which determines the completion. Thus, this sensor device preferably notifies to the other sensor device(s) of the tracking system that the next step is to be performed. This may result in one or more of the sensor devices to change its function from being a marker device to being a marker detection device or vice versa. In addition, a sensor device may display on its display 4 some guidance information on what to do in the next workflow step, thus leading the operator of the tracking system through the workflow.

A sensor device 1, 2 may further comprise an acceleration sensor (not shown). When the sensor data of the acceleration sensor is integrated over a period of time, this results in an information on the change of the position of the sensor device in this period of time. This information may also be exchanged between the sensor devices and used for calculating the relative position between the sensor devices.

It is to be noted that the methods and workflows described herein do not relate to or comprise any surgical step. In particular, attaching a cutting block to a bone and performing a cut are not part of the present invention. This invention solely relates to the step of navigating, tracking and verifying by acquiring and analyzing data.

Any embodiment described so far may be combined with one or more features of the following additional embodiments, wherein a position sensor is a marker device detector:

Embodiment 1: A medical tracking system comprising at least two sensor devices (1, 2) which are independently maneuverable and can be positioned in a fixed position relative to targets (10, 13, 15), each sensor device (1, 2) comprising at least one of an orientation sensor (5) and a position sensor (6, 7) for respectively determining sensor data, the system further comprising a control unit (3) configured to receive and combine the at least two sensor data of the at least two sensor devices (1, 2) in order to determine a relative position between at least two of the at least two sensor devices (1, 2).

Embodiment 2: The tracking system of embodiment 1, wherein the at least two sensor data represent insufficient information for determining the relative position between the at least two sensor devices (1, 2).

Embodiment 3: The tracking system of embodiment 1 or 2, wherein the at least two sensor data respectively are data describing the relative position between the respective sensor device (1, 2) and a relative position reference (18).

Embodiment 4: The tracking system of one of embodiments 1 to 3, wherein the control unit (3) is located in one of the sensor devices (1, 2), each sensor device (1, 2) comprises a control unit (3) or each sensor device (1, 2) comprises a part of the control unit (3).

Embodiment 5: The tracking system of any one of embodiments 1 to 4, further comprising at least one marker (12) attached to at least one of the sensor devices (1, 2).

Embodiment 6: The tracking system according to any one of embodiments 1 to 5, wherein at least one of the sensor devices (1, 2) comprises an orientation sensor (5) and the control unit (3) is configured to convert orientation data of an orientation sensor (5) into a coordinate system determined by a target (9, 10) to which one of the sensor devices (1, 2) is attached.

Embodiment 7: The tracking system according to any one of embodiments 1 to 6, wherein a position sensor (6, 7) comprises a still or video camera and/or at least one of the sensor devices (1, 2) comprises an orientation sensor (5) and a position sensor (6, 7) and/or at least one of the at least two sensor devices (1, 2) comprises an acceleration sensor.

Embodiment 8: The tracking system of embodiment 7, wherein a position sensor comprises a distance sensor (19) comprising a laser beam source, wherein the laser beam is angled compared to the optical axis of the camera.

Embodiment 9: The tracking system of any one of embodiments 1 to 8, wherein a position sensor (6, 7) is a marker device detector, the sensor device (1, 2) comprises a marker device (9, 14) and the control unit (3) is configured to select the function of the sensor device (1, 2) as either acting as a marker device detector or as a marker device in a step of the medical navigation workflow.

Embodiment 10: A method of determining a relative position between two sensor devices (1, 2) of a medical tracking system, wherein the sensor devices (1, 2) are independently maneuverable and can be positioned in a fixed position relative to targets (10, 13, 15), comprising the steps of determining sensor data comprising at least one of orientation data and position data with two or more of the sensor devices (1, 2)

transferring the sensor data to a control unit (3) and determining the relative position between two sensor devices (1, 2) by the control unit (3) by combining the sensor data.

Embodiment 11: The method of embodiment 10, wherein each sensor device (1, 2) is attached to a target (10, 13, 15) and the relative position of the targets (10, 13, 15) is determined from the relative position of the sensor devices (1, 2).

Embodiment 12: The method of embodiment 10 or 11, characterized by using a sensor device (1, 2) comprising a marker device (9, 14) and a position sensor being a marker device detector (6, 7) as a marker device detector in one step of the medical navigation workflow for obtaining information for determining the position of a marker device (9, 14)

and using the same sensor device (1, 2) as a marker device in another step of the medical navigation workflow.

Embodiment 13: A method for determining a mechanical property of a joint between two bones, comprising the steps of:
  positioning a first sensor device (1) in a fixed position relative to the first bone (T),
  registering the first bone (T) by sampling a plurality of sample points using a pointer (13) and the first sensor device (1),
  positioning a second sensor device (2) in a fixed position relative to the second bone (F),
  registering the second bone (T) by sampling a plurality of sample points using a pointer (13) and the second sensor device (2),
  optionally re-positioning the first sensor device (1) in its fixed position relative to the first bone (T) if the first sensor device was used as a marker device of the pointer in the previous step,
  determining at least one relative position between the first sensor device (1) and the second sensor device (2) for at least one position of the joint as described in embodiment 10 and
  determining the mechanical property of the joint between the first bone (T) and the second bone (F) from the at least one relative position between the first sensor device (1) and the second sensor device (2).

Embodiment 14: A method for aiding the adjustment an adjustable cutting block (10, 15) comprising a base (11, 16) and a cutting slot (12, 17) which is adjustable relative to the base (11, 16), the base (11, 16) being attached to a bone (T, F), comprising the steps of
  positioning a first sensor device (1) in a fixed position relative to the cutting slot (12, 17),
  registering the bone (T, F) by sampling a plurality of sample points using a pointer (13) and the first sensor device (1) such that the initial alignment of the cutting slot (12, 17) relative to the bone (T, F) is known,
  positioning a second sensor device (2) in a fixed position relative to the base (11, 16) of the cutting block (10, 15),
  determining the relative position between the first sensor device (1) and the second sensor device (2) as described in embodiment 10 for the initial alignment of the cutting slot (12, 17),
  determining the relative position between the first sensor device (1) and the second sensor device (2) as described in embodiment 10 while the cutting slot (12, 17) is adjusted and
  determining the current alignment of the cutting slot (12, 17) from the initial alignment of the cutting slot (12, 17) and the current relative position between the first sensor device (1) and the second sensor device (2).

Preferably, the sensor data provided by a single sensor device is not sufficient for determining all parameters for all desired dimensions of the relative position. In other words, the sensor data of a single sensor device is not sufficient to determine the desired number of parameters of the relative position. In yet other words, the sensor data of a single sensor device describe insufficient information on the relative position. The number of parameters which can be determined from the sensor data of a single sensor device might be less than the desired number of parameters, or the determination of a parameter might require more than the information given by the sensor data of a single sensor device. However, if the sensor data of two or more sensor devices is combined, the available information (also referred to as sufficient information) is sufficient to determine all parameters for all desired dimensions of the relative position. Preferably, the available information is more than sufficient, such that the information is overdetermined. In this case, the sensor data is also understood as representing sufficient information. This can be used for increasing the quality of the determined relative position.

The invention claimed is:

1. A medical tracking system comprising:
  a first navigation sensor device which can be positioned in a fixed position relative to an associated target, the first navigation sensor device comprising a first housing, the first navigation sensor device selectively behaving as either of a first marker device or as a first marker device detector capable of obtaining information for determining a relative position between the first marker device detector and an associated second marker device of an associated second navigation sensor device different than the first navigation sensor device; and
  a first control unit configured to process a medical navigation workflow and to select, based on a first step of the medical navigation workflow, a function of the first navigation sensor device as either:
    behaving as the marker device detector in the first step of the medical navigation workflow, or
    behaving as the marker device in the first step of the medical navigation workflow,
  wherein the first navigation sensor device selectively behaves as the first marker device by displaying in the first step of the medical navigation workflow optical markers comprising a plurality of optically detectable markers operatively coupled with the first housing and disposed in a predetermined spatial relationship relative to each other, wherein the first navigation sensor device selectively behaves as the marker device detector by imaging in the first step of the medical navigation workflow one or more markers displayed by the associated second marker device of the associated second navigation sensor device different than the first navigation sensor device,
  wherein the first control unit is configured to determine a completion of the first step of the medical navigation workflow,
  wherein the first control unit is configured to transmit an instruction signal to the associated second navigation sensor device responsive to determining the completion of the first step of the medical navigation workflow, the instruction signal instructing the associated second navigation sensor device to initiate performing a second step of the medical navigation workflow,
  wherein the first navigation sensor device is configured to act as having pointer functionality when the first navigation sensor device is behaving as the marker device in the first step of the medical navigation workflow.

2. The tracking system of claim 1, wherein the first navigation sensor device comprises a display for displaying at least a part of the optical markers of the first marker device.

3. The tracking system of claim 1, wherein the optical markers of the first marker device comprises a plurality of squares in a known configuration.

4. The tracking system of claim 1, further comprising the associated second navigation sensor device, wherein, in the first step of the medical navigation workflow:
  the second navigation sensor device behaves as the marker device and the first navigation sensor device behaves as the marker device detector; or the first navigation sensor device behaves as the marker device and the second navigation sensor device behaves as the marker device detector.

5. The tracking system of claim 4, wherein the second navigation sensor device is configured to act as having pointer functionality when the first navigation sensor device is positioned in the fixed position relative to the associated target.

6. The tracking system of claim 4, wherein:
the first navigation sensor device or the second navigation sensor device behaving as the marker device is configured to transmit output data of its marker device detector, an orientation sensor or an acceleration sensor as marker sensor data to the control unit;
the first navigation sensor device or the second navigation sensor device behaving as the marker detection device is configured to transmit output data of its marker detection device as detection sensor data to the control unit; and
the control unit is configured to receive and combine the marker sensor data and the detection sensor data of the first and second navigation sensor devices to determine a relative position between the first and second navigation sensor devices.

7. The tracking system according to claim 1, wherein the first navigation sensor device comprises an orientation sensor.

8. A method of medical tracking for supporting a medical navigation workflow, the method comprising:
using a first navigation sensor device comprising a first housing to behave in a first step of a medical navigation workflow as a first marker device detector obtaining information for determining a position of an associated second optical marker device of an associated second navigation sensor device different than the first navigation sensor device;
using the first navigation sensor device to determine a completion of the first step of the medical navigation workflow;
using the first navigation sensor device to transmit an instruction signal to the associated second navigation sensor device responsive to determining the completion of the first step of the medical navigation workflow, the instruction signal instructing the associated second navigation sensor device to initiate performing a second step of the medical navigation workflow, the second step of the medical navigation workflow being different than the first step of the medical navigation workflow; and
using the first navigation sensor device to behave in the second step of the medical navigation workflow as an optical marker device displaying one or more optical markers for use by the associated second navigation sensor device to obtain information for determining by the associated second navigation sensor device a position of the first navigation sensor device,
wherein the first navigation sensor device behaves in the first and second steps of the medical navigation workflow as either:
the first marker device detector, or
the optical marker device,
wherein the first navigation sensor device is configured to act as having pointer functionality when the first navigation sensor device behaves in the second step of the medical navigation workflow as the optical marker device displaying the one or more optical markers.

9. The method according to claim 8, wherein:
both the first and associated second navigation sensor devices are used;
the first navigation sensor device behaves as the optical marker device of a pointer for pointing at sample points of an associated target; and
the associated second navigation sensor device is configured to be positioned in a fixed position relative to the associated target, and to behave as the marker device detector for obtaining information for determining a position of the first optical marker device.

10. The method according to claim 9, further comprising registering the associated target by sampling a plurality of the sample points.

11. The method of claim 9, wherein:
the first navigation sensor device behaving as the optical marker device and the associated second navigation sensor device behaving as the marker device detector both comprise using an orientation sensor to generate orientation sensor data used for determining the position of the optical marker device.

12. The method of claim 8, further comprising:
determining sensor data comprising at least one of orientation data, position data and/or acceleration data with the first and associated second navigation sensor devices transferring the sensor data to a selected control unit; and
determining the relative position between the first and associated second or more navigation sensor devices by the selected control unit by combining the sensor data.

13. The method of claim 8, wherein the associated second navigation sensor device further comprises a display device and is positioned in a fixed position relative to a bone, wherein the first navigation sensor device behaving as the first marker device detector comprises a still camera or a video camera behaving as the first marker device detector, wherein an image captured by the one or more of the still camera and/or the video camera is displayed on the display device and a characteristic property of the bone can be input based on the camera image on the display device.

14. A non-transitory computer readable storage medium comprising a computer program which, when running on a computer or when loaded onto a computer, causes the computer to perform a method comprising:
using a first navigation sensor device comprising a first housing to behave in a first step of a medical navigation workflow as a first marker device detector obtaining information for determining a position of an associated second optical marker device of an associated second navigation sensor device different than the first navigation sensor device;
using the first navigation sensor device to determine a completion of the first step of the medical navigation workflow;
using the first navigation sensor device to transmit an instruction signal to the associated second navigation sensor device responsive to determining the completion of the first step of the medical navigation workflow, the instruction signal instructing the associated second navigation sensor device to initiate performing a second step of the medical navigation workflow, the second step of the medical navigation workflow being different than the first step of the medical navigation workflow;
using the first navigation sensor device to behave in the second step of the medical navigation workflow as a first optical marker device displaying one or more optical markers for use by the associated second navigation sensor device behaving as a second marker device detector to obtain information for determining by the associated second navigation sensor device a position of the first navigation sensor device, wherein the first navigation sensor device behaves in the first and second steps of the medical navigation workflow as either:

the first marker device detector, or the optical marker device, wherein the first navigation sensor device is configured to act as having pointer functionality when the first navigation sensor device behaves as the optical marker device.

15. The tracking system of claim 4, wherein:

the first marker device detector is the first navigation sensor device behaving as the marker device detector; and the first marker device is the first navigation sensor device behaving as the marker device.

16. The method of claim 9, wherein:

the first marker device detector is the first navigation sensor device behaving as the marker device detector; and the first marker device is the first navigation sensor device behaving as the marker device.

17. The non-transitory computer readable storage medium according to claim 14, wherein:

both the first navigation sensor device and the associated second navigation sensor device are used, the first navigation sensor device acts as having the optical marker device functionality of a pointer for pointing at sample points of an associated target, and the associated second navigation sensor device is configured to be positioned in a fixed position relative to the associated target, and to act as having the marker device detector functionality for obtaining information for determining the position of the first optical marker device.

18. The non-transitory computer readable storage medium according to claim 17, wherein:

the first marker device detector is the first navigation sensor device behaving as the marker device detector; and the first marker device is the first navigation sensor device behaving as the marker device.

19. The method according to claim 8, further comprising:

switching between the behaving as the optical marker device of the first navigation sensor device and the behaving as the marker device detector of the first navigation sensor device in accordance with the first step and the second step of the medical navigation workflow.

20. The tracking system of claim 1, wherein the first control unit is configured to determine the completion of the first step of the medical navigation workflow in accordance with a completion signal received at an input of the tracking system from an associated human operator of the medical tracking system.

21. The tracking system of claim 2, wherein:

the first navigation sensor device comprises a display; and the first control unit is configured to generate, on the display, operator instructions responsive to determining the completion of the first step of the medical navigation workflow, the operator instructions comprising guidance information for use by an associate human operator of the tracking system for performing the second step of the medical navigation workflow.

22. The tracking system of claim 1, wherein:

the first control unit is configured to select, based on the second step of the medical navigation workflow, the function of the first navigation sensor device as either:

behaving as the marker device detector in the second step of the medical navigation workflow, or behaving as the marker device in the second step of the medical navigation workflow.

23. The tracking system of claim 22, wherein:

the first control unit is configured to select, based on the first step of the medical navigation workflow, the function of the first navigation sensor device as behaving as the marker device detector in the first step of the medical navigation workflow; and the first control unit is configured to select, based on the second step of the medical navigation workflow, the function of the first navigation sensor device as behaving as the marker device in the second step of the medical navigation workflow.

24. The tracking system of claim 22, wherein:

the first control unit is configured to select, based on the first step of the medical navigation workflow, the function of the first navigation sensor device as behaving as the marker device in the first step of the medical navigation workflow; and the first control unit is configured to select, based on the second step of the medical navigation workflow, the function of the first navigation sensor device as behaving as the marker device detector in the second step of the medical navigation workflow.

* * * * *